US009339182B2

United States Patent
Chen et al.

(10) Patent No.: US 9,339,182 B2
(45) Date of Patent: May 17, 2016

(54) EYE IMAGING SYSTEM

(71) Applicant: Shanghai Mediworks Precision Instruments Co., Ltd., Shanghai (CN)

(72) Inventors: Wenguang Chen, Shanghai (CN); Sufeng Yan, Shanghai (CN); Yue Wei, Shanghai (CN); Zhaosong Kong, Shanghai (CN)

(73) Assignee: SHANGHAI MEDIWORKS PRECISION INSTRUMENTS CO., LTD., Shanghai (CN)

( * ) Notice: Subject to any disclaimer, the term of this patent is extended or adjusted under 35 U.S.C. 154(b) by 145 days.

(21) Appl. No.: 14/159,488

(22) Filed: Jan. 21, 2014

(65) Prior Publication Data

US 2014/0132921 A1 May 15, 2014

Related U.S. Application Data

(63) Continuation-in-part of application No. PCT/CN2012/078962, filed on Jul. 20, 2012.

(30) Foreign Application Priority Data

Jul. 21, 2011 (CN) .......................... 2011 1 0204369

(51) Int. Cl.
A61B 3/14 (2006.01)
A61B 3/12 (2006.01)
A61B 3/00 (2006.01)
A61B 3/15 (2006.01)

(52) U.S. Cl.
CPC .................. *A61B 3/12* (2013.01); *A61B 3/0008* (2013.01); *A61B 3/14* (2013.01); *A61B 3/156* (2013.01)

(58) Field of Classification Search
CPC .......... A61B 3/0008; A61B 3/12; A61B 3/14; A61B 3/145; A61B 3/15; A61B 3/156; A61B 3/158
USPC .................................. 351/205, 206, 210, 221
See application file for complete search history.

(56) References Cited

U.S. PATENT DOCUMENTS

2011/0273669 A1* 11/2011 Abitbol et al. ................ 351/212

* cited by examiner

*Primary Examiner* — Huy K Mai
(74) *Attorney, Agent, or Firm* — Matthias Scholl, PC; Matthias Scholl

(57) ABSTRACT

An eye imaging system, including: a light source module; a radial splitting module; a common optical module; an image receiver; a power supply module for the light source module; a driver module for the image receiver; a processing-displaying module; and a motion driving module. The image receiver is an area array sensor. The motion driving module is connected to the light source module and drives the light source module to move in a radial direction of an upstream illuminating optical path formed by the light source module and the radial splitting module. The image receiver continually opens for exposure in a radial direction of a downstream observation optical path formed by the radial splitting module and the image receiver. The continual opening of the image receiver for signal acquisition is synchronous with the movement of the light source module.

11 Claims, 6 Drawing Sheets

EYE IMAGING SYSTEM

CROSS-REFERENCE TO RELATED APPLICATIONS

This application is a continuation-in-part of International Patent Application No. PCT/CN2012/078962 with an international filing date of Jul. 20, 2012, designating the United States, now pending, and further claims priority benefits to Chinese Patent Application No. 201110204369.0 filed Jul. 21, 2011. The contents of all of the aforementioned applications, including any intervening amendments thereto, are incorporated herein by reference. Inquiries from the public to applicants or assignees concerning this document or the related applications should be directed to: Matthias Scholl P. C., Attn.: Dr. Matthias Scholl Esq., 14781 Memorial Drive, Suite 1319, Houston, Tex. 77079.

BACKGROUND OF THE INVENTION

1. Field of the Invention

The invention relates to an eye imaging system.

2. Description of the Related Art

A typical optical instrument for eye detection or imaging includes a lighting optical path and an observation optical path. The lighting optical path is used to illuminate the eye of the observed, and a reflected light ray from the eye passes through the observation optical path to illuminate on the eye of the observer or an observation device, so that the healthy condition of the eye including fundus is observed and photographed.

However, the eye structure is complicated and the specific physiological tissues vary from one patient to another. Particularly, when using an optical instrument to observe and photograph, surplus reflected light of the cornea and the surface of the objective lens passes through the optical instrument and forms a ghost image. Therefore, the quality of the overall image of observation is lowered, and it becomes necessary to eliminate the ghost image and various stray lights in the optical system.

Conventional ophthalmic optical instruments often employ a black pot plate or an annular aperture to eliminate the ghost image and the stray lights. Specifically, these instruments have the following disadvantages:

1. The ghost image and the stray lights cannot be completely eliminated, and the obtained image quality is poor.
2. The lighting optical path and the observation optical path are independent from each other, and the production cost is relatively high.
3. Optical structures designed for eliminating the ghost image and the stray lights has a relatively complicate structure and occupies large volume.
4. When annular aperture is employed, the availability of the light source is relatively low while the energy consumption is relatively large.
5. The light flux entering the eye of the patient is relatively high, which results in patient discomfort.

Thus, an eye imaging system that has a high imaging quality, relatively simple structure, low production cost, and energy consumption, good effect on elimination of ghost image, and little by-effect on the eye of the patient is desired.

SUMMARY OF THE INVENTION

In view of the above-described problems, it is one objective of the invention to provide an eye imaging system that overcomes the above shortages and has practical functions and good performance.

To achieve the above objective, in accordance with one embodiment of the invention, there is provided an eye imaging system, comprising: a light source module; a radial splitting module; a common optical module; an image receiver; a power supply module for the light source module; a driver module for the image receiver; a processing-displaying module; and a motion driving module. The image receiver is an area array sensor. The motion driving module is connected to the light source module and drives the light source module to move in a radial direction of an upstream illuminating optical path formed by the light source module and the radial splitting module; while the image receiver continually opens for exposure in a radial direction of a downstream observation optical path formed by the radial splitting module and the image receiver. The continual opening of the image receiver for signal acquisition is synchronous with the motion of the light source module.

In a class of this embodiment, the light source module is disposed on a lateral face of a common optical path formed by the common optical module and the radial splitting module. The image receiver is disposed on an optical path of a light ray sent back by the common optical module after being refracted by the optical module. The light ray sent out by the light source module is reflected by the radial splitting module and scans an eye via the common optical module. A reflected light ray passes through the common optical module, and reaches the image receiver after being refracted by the radial splitting module; and the image receiver is totally or partially exposed.

In a class of this embodiment, the light source module is disposed on a front face of a common optical path formed by the common optical module and the radial splitting module. The image receiver is disposed on an optical path of a light ray sent back by the common optical module after being reflected by the radial splitting module. The light ray sent out by the light source module is refracted by the radial splitting module and scans an eye via the common optical module. A reflected light ray passes through the common optical module, and reaches the image receiver after being reflected by the radial splitting module; and the image receiver is totally or partially exposed.

In a class of this embodiment, the image receiver, the driver module for the image receiver, and the processing-displaying module are in signal connection in order. The processing-displaying module is capable of stitching electric signals of core exposure region sent by the driver module for the image receiver for forming a complete or partial eye image in a larger region, and processing, recording, or displaying the eye image.

In a class of this embodiment, the light source module and the image receiver moves at a uniform velocity whereby achieving uniform illumination, uniform exposure, and uniform imaging of the eye.

In a class of this embodiment, the light source module moves in one direction or reciprocates.

In a class of this embodiment, the motion driving module and the processing-displaying module are in signal connection. The processing-displaying module is capable of controlling the motion driving module to drive the light source module to move.

In a class of this embodiment, the light source module comprises a light source device, and a total of or part of a condenser group, a dodging device, and an illumination diaphragm.

In a class of this embodiment, an emergent light of the light source module is capable of forming a ribbon light source.

In a class of this embodiment, the radial splitting module is a beam splitter prism or a planar spectroscope for reflecting and refracting the light ray at a certain ratio.

In a class of this embodiment, the common optical module comprises a relay lens and an eye-contact lens.

In a class of this embodiment, the light rays sent out by the light source module passes through the radial splitting module and the common optical module to illuminate and scan a fundus of the eye.

The test results of the eye imaging system of the invention show that, stray light hardly exists in the light ray after being reflected and reaching the image receiver, thereby preventing the formation of the ghost image.

Advantages of the invention are summarized as follows:

1. The movable light source module is employed, the scanning is realized by a small beam of light, and surplus light rays are prevented from illuminating the eye parts not required to be exposed contemporarily by using the narrow gap. Thus, the possible surplus stray lights are eliminated from the source, thereby acquiring a good observation and high quality of image.

2. The image receiver continually opens for exposure, so that the exposure by a small beam and signal read and conversion of a small core area are realized. Surplus stray lights formed by various diffuse reflections and system errors are eliminated upon passing the optical instrument and the eye, thereby further ensuring the image quality.

3. The illumination and the optical path for observation and imaging are realized based on the common optical path.

4. Optical devices are seldom employed, so that the eye imaging system is easy for realization and the production cost is low.

5. The eye imaging system of the invention is easy for control, and the error is controlled within a small range.

6. Relatively few light rays are required, so that the power consumption and heat dissipation of the light source are lowered by a certain level.

7. The ribbon light source is employed to illuminate eyes of a patient. As the light flux entering the eyes of the patient is largely lowered, the stimulation of the light rays on the eyes of the patient is eliminated, thereby enabling the patient to feel comfortable during the eye inspection.

BRIEF DESCRIPTION OF THE DRAWINGS

The invention is described hereinbelow with reference to the accompanying drawings, in which.

Figure 1:
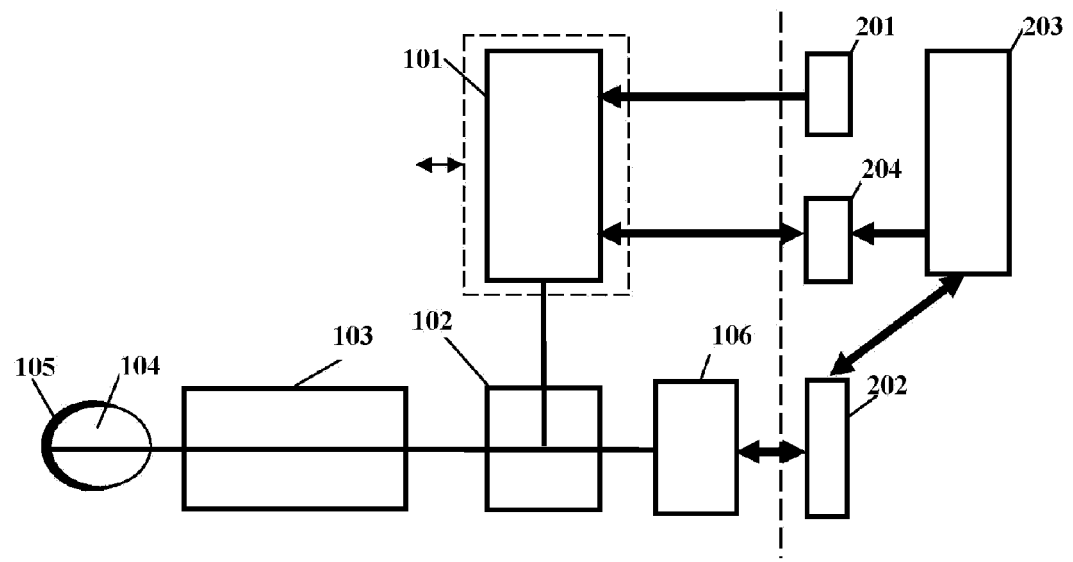
FIG. 1 is a schematic diagram of an eye imaging system in accordance with one embodiment of the invention.

In the drawings, the following reference numbers are used: 101. Light source module; 102. Radial splitting module; 103. Common optical module; 104. Eye; 105. Fundus; 106. Image receiver; 100. Core scanning region; 201. Power supply module for light source module; 202. Driver module for image receiver; 203. Processing-displaying module; 204. Motion driving module; 200. Core exposure region; and 300. Image of eye.

DETAILED DESCRIPTION OF THE EMBODIMENTS

For further illustrating the invention, experiments detailing an eye imaging system are described below. It should be noted that the following examples are intended to describe and not to limit the invention.

As shown in FIG. 1, a schematic diagram of an eye imaging system of the invention comprises: a light source module 101; a radial splitting module 102; a common optical module 103; an image receiver 106; a power supply module 201 for the light source module; a driver module 202 for the image receiver; a processing-displaying module 203; and a motion driving module 204.

The motion driving module 204 is connected to the light source module 101 and drives the light source module 101 to move in a radial direction of an upstream illuminating optical path formed by the light source module 101 and the radial splitting module 102; while the image receiver 106 continually opens for exposure in a radial direction of a downstream observation optical path formed by the radial splitting module 102 and the image receiver 106. The continual opening of the image receiver for signal acquisition is synchronous with the motion of the light source module 101.

The light source module 101 comprises a light source device, and a total of or part of a condenser group, a dodging device, and an illumination diaphragm. An emergent light of the light source module 101 is capable of forming a ribbon light source. The radial splitting module 102 is a beam splitter prism or a planar spectroscope. For those skilled in the art, other spectroscopic devices can be employed to reflect and refract the light ray at a certain ratio. The common optical module 103 comprises a relay lens 1032 and an eye-contact lens 1031.

The image receiver 106, the driver module 202 for the image receiver, and the processing-displaying module 203 are in signal connection in order. The processing-displaying module 203 is capable of stitching electric signals of core exposure region 200 sent by the driver module 202 for forming a complete or partial eye image 300 in a larger region, and processing, recording, or displaying the eye image.

The light source module 101 and the image receiver 106 moves at a uniform velocity whereby achieving uniform illumination, uniform exposure, and uniform imaging of the eye. The light source module 101 moves in one direction or reciprocates. The motion driving module 204 and the processing-displaying module 203 are in signal connection. The processing-displaying module 203 is capable of controlling the motion driving module 204 to drive the light source module 101 to move.

Preferably, the light sent out by the light source module 101 passes through the radial splitting module 102 and the common optical module 103 to illuminate and scan a fundus 105 of the eye. That is, the system of the invention is suitable for inspection or photographing of different parts of the eye 104, and is particularly used in fundus inspection or photographing.

The above technical solution is applicable to the following Examples.

Figure 2:
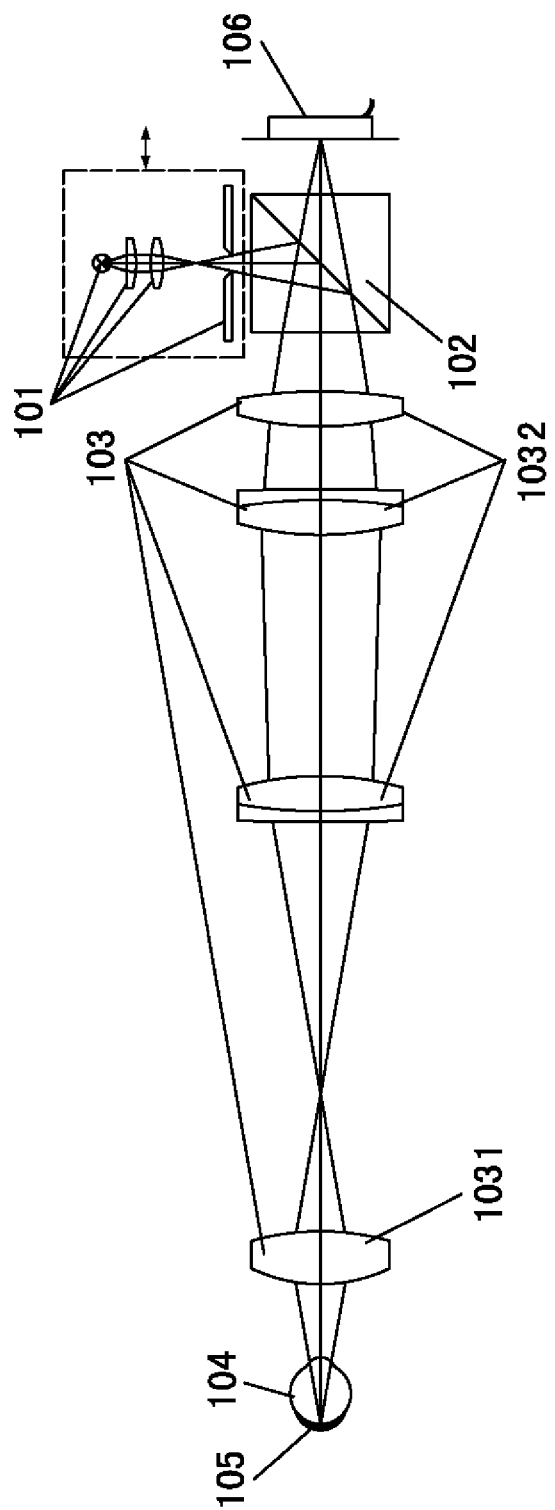
FIG. 2 is a schematic diagram of part of an optical path comprising a light source module arranged on a lateral face of a common optical path in accordance with one embodiment of the invention.

A diagram of part of optical path having the light source module arranged on a lateral face of the optical path is shown in FIG. 2. The light source module 101 is disposed on a lateral face of a common optical path formed by the common optical module 103 and the radial splitting module 102. The image receiver 106 is disposed on an optical path of a light ray sent back by the common optical module 103 after being refracted by the optical module 102. The light ray sent out by the light source module 101 is reflected by the radial splitting module 102 and scans an eye 104 via the common optical module 103. A reflected light ray passes through the common optical module 103, and reaches the image receiver 106 after being refracted by the radial splitting module 102, and the image receiver 106 is totally or partially exposed.

Figure 3:
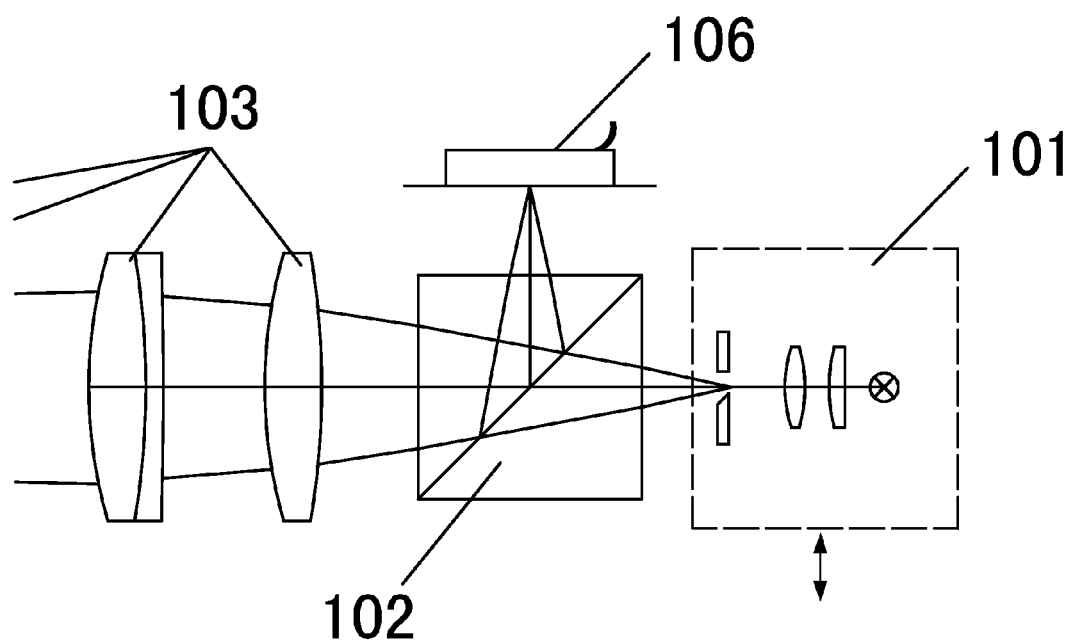
FIG. 3 is a schematic diagram of part of an optical path comprising a light source module arranged on a front face of a common optical path in accordance with one embodiment of the invention.

A diagram of part of optical path having the light source module arranged on a front face of the optical path is shown in FIG. 3, the light source module 101 is disposed on a front face of a common optical path formed by the common optical module 103 and the radial splitting module 102. The image receiver 106 is disposed on an optical path of a light ray sent back by the common optical module 103 after being reflected by the radial splitting module 102. The light ray sent out by the light source module 101 is refracted by the radial splitting module 102 and scans an eye 104 via the common optical module 103; a reflected light ray passes through the common optical module 103, and reaches the image receiver 106 after being reflected by the radial splitting module 102, and the image receiver 106 is totally or partially exposed.

Figure 4:
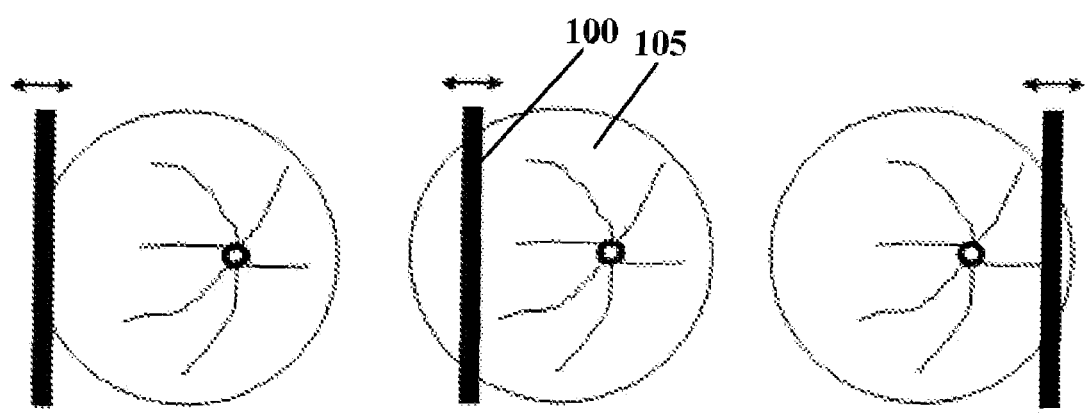
FIG. 4 is an illumination and scanning diagram of a front face of a fundus in accordance with one embodiment of the invention.

FIG. 4 indicates the process for conducting the scanning of the fundus 105 by the illuminating and scanning light rays, and a band scanning is preferably shown. It is ensured that as few light ray as possible illuminates part of as small fundus 105 as possible in each moment, and it is clearly shown in FIG. 4 that almost no stray light illuminates the fundus 105. Other parts on two sides of the fundus are scarcely illuminated.

Figure 5:
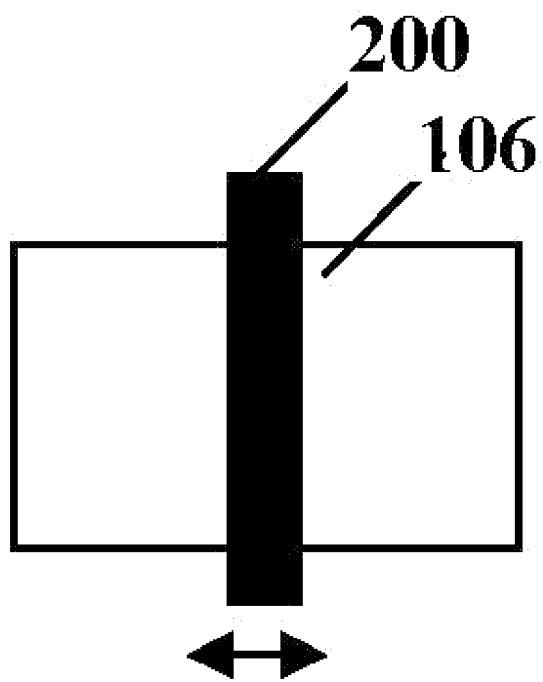
FIG. 5 is a schematic diagram of imaging by a ribbon light when an area array sensor is totally exposed in accordance with one embodiment of the invention.

As shown in FIG. 5, when the image receiver 106 is an area array sensor, the image receiver can be completely exposed to form a core exposure region 200. A subsequent reading of the electric signals converted by the image receiver 106 only reads the core exposure region 200. Light rays out of the core scanning region of the eye 104 from other directions transmitted by diffuse reflections is screened, and stray lights of the optical system itself is eliminated.

Figure 6:
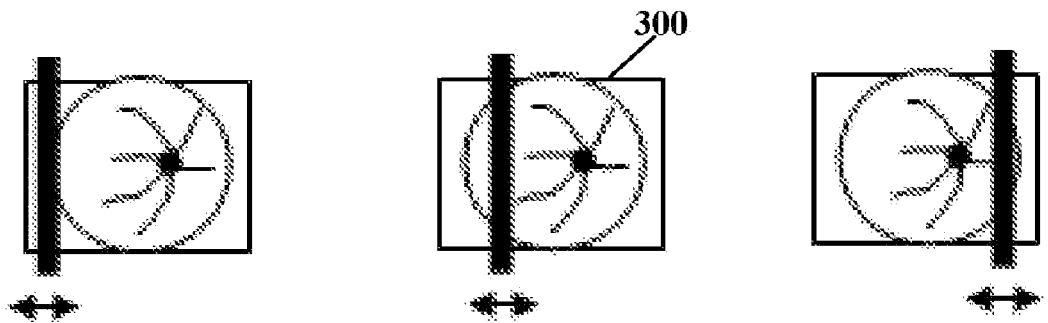
FIG. 6 is a schematic diagram of a final image displayed by a processing-displaying module.

FIG. 6 shows the image of eye 300 stitched by the processing-displaying module 203 and schematically indicates that a new complete frame of image of eye 300 in the absence of ghost image is formed by a combination of several exposed bands of multi-frame images in the absence of ghost image.

While particular embodiments of the invention have been shown and described, it will be obvious to those skilled in the art that changes and modifications may be made without departing from the invention in its broader aspects, and therefore, the aim in the appended claims is to cover all such changes and modifications as fall within the true spirit and scope of the invention.

The invention claimed is:

1. An eye imaging system for imaging an eye of a user, the eye having a width, the eye imaging system comprising:
    a) a light source module;
    b) a splitting module;
    c) a common optical module;
    d) an image receiver;
    e) a power supply module;
    f) a driver module;
    g) a processing-displaying module; and
    h) a motion driving module;
wherein:
    the image receiver is an area array sensor;
    the light source module is adapted to generate a first light beam having a width substantially smaller than the width of the eye;
    the common optical module and the splitting module form a first optical path;
    the splitting module splits the first light beam into a second light beam and a third light beam;
    the second light beam transmits along the first optical path, reaches the eye, and illuminates part of the eye;
    the third light beam transmits along a second optical path perpendicular to the first optical path;
    the light source module is disposed on the first optical path and the image receiver is disposed on the second optical path, or the light source module is disposed on the second optical path and the image receiver is disposed on the first optical path;
    the motion driving module is connected to the light source module and drives the light source module to move, wherein when the light source module moves, the second light beam moves in a direction perpendicular to an optical axis of the eye;
    the image receiver opens and closes continually when the light source module moves, wherein when the image receiver opens, the image receiver receives a plurality of partial images of the eye; and
    the processing-displaying module combines the plurality of partial images of the eye and forms an overall image of the eye.

2. The system of claim 1, wherein:
    the image receiver, the driver module, and the processing-displaying module are in connection in order; and
    the processing-displaying module is adapted to process, record, or display the overall image of the eye.

3. The system of claim 1, wherein the light source module moves at a constant speed.

4. The system of claim 1, wherein the light source module moves in one direction or reciprocates.

5. The system of claim 1, wherein:
    the motion driving module and the processing-displaying module are in connection; and
    the processing-displaying module is adapted to drive the motion driving module to move the light source module.

6. The system of claim 1, wherein the light source module comprises a light source device, a condenser group, a dodging device, and an illumination diaphragm.

7. The system of claim 1, wherein the light source module is adapted to form a ribbon light.

8. The system of claim 1, wherein the splitting module is a beam splitter prism or a planar spectroscope.

9. The system of claim 1, wherein the common optical module comprises a relay lens and an eye-contact lens.

10. The system of claim 1, wherein the splitting module splits the first light beam into the second light beam that illuminates part of a fundus of the eye and the third light beam.

11. A method of imaging an eye of a user, the method comprising:
    generating a first light beam having a width substantially smaller than the width of the eye by a light source module;
    splitting the first light beam into a second light beam and a third light beam by a splitting module;

transmitting the second light beam along a first optical path to reach the eye and illuminate part of the eye;
transmitting the third light beam along a second optical path perpendicular to the first optical path;
moving the second light beam in a direction perpendicular to an optical axis of the eye by a motion driving module;
forming a plurality of partial images of the eye by continually opening and closing an image receiver to receive the third light beam; and
combining the plurality of partial images of the eye and forming an overall image of the eye by using a processing-displaying module.

\* \* \* \* \*